United States Patent [19]
Kobayashi et al.

[11] Patent Number: 5,002,884
[45] Date of Patent: Mar. 26, 1991

[54] IMMOBILIZATION OF PHYSIOLOGICALLY ACTIVE SUBSTANCES ON AN INORGANIC SUPPORT

[75] Inventors: Hideki Kobayashi, Ichihara; Tadashi Matsunaga, Fuchu, both of Japan; Hideki Kobayashi, Midland, Mich.

[73] Assignee: Toray Silicon Company, Ltd., Tokyo, Japan

[21] Appl. No.: 297,793

[22] Filed: Jan. 17, 1989

[30] Foreign Application Priority Data

Jan. 18, 1988 [JP] Japan .................... 63-768088

[51] Int. Cl.$^5$ .................. C12N 11/14; C12N 11/06; G01N 33/551; G01N 33/549
[52] U.S. Cl. ................... 435/176; 435/181; 436/524; 436/525; 436/527; 436/532; 530/811
[58] Field of Search ............ 435/174, 176, 181; 436/524, 525, 527, 532; 530/811

[56] References Cited
U.S. PATENT DOCUMENTS 3,652,761  3/1972  Weetall ........................ 424/12
3,669,841  6/1972  Miller ......................... 435/176
4,098,840  7/1978  Yoshida et al. ............. 526/263 X
4,683,203  7/1987  Anton et al. ................ 435/176 X

OTHER PUBLICATIONS

Chemical Abstracts, vol. 102, No. 19, May 13, 1985, p. 325, No. 163353f.

Primary Examiner—David M. Naff
Attorney, Agent, or Firm—Jim L. DeCesare

[57] ABSTRACT

Physiologically active substances are immobilized on an inorganic support, by treating the inorganic support with an aminoalkylakoxysilane having the general formula

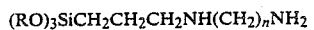

$(RO)_3SiCH_2CH_2CH_2NH(CH_2)_nNH_2$ wherein, R is an alkyl group having 1 to 4 carbon atoms, and n is an integer having a value of 5 to 12, and chemically bonding a physiologically active substance by means of an amino group to the support.

7 Claims, No Drawings

IMMOBILIZATION OF PHYSIOLOGICALLY ACTIVE SUBSTANCES ON AN INORGANIC SUPPORT

BACKGROUND OF THE INVENTION

The present invention relates to a method for the immobilization or fixation of physiologically active substances, more specifically, to the immobilization or fixation of physiologically active substances on inorganic carriers or supports.

With respect to prior methods for the immobilization of physiologically active substances on inorganic carriers or supports, methods are known which afford a more stable immobilization than simple physical adsorption. For example, the prior methods are shown in U.S. Pat. No. 3,652,761, Japanese Patent Application No. 54-73185 [73,185/79], and Japanese Patent Application No. 60-232090 [232,090/85]. These methods are for the immobilization of physiologically active substances by the procedure of treating the surface of an inorganic support with 3-aminopropyltriethoxysilane or N-(2-aminoethyl)-3-aminopropyltrimethoxysilane, with the amino group as an attachment point.

In order for a physiologically active substance to develop its activity, it is essential that the specific higher order structure encompassing the active center be preserved.

In the immobilization and use of physiologically active substances, higher order structures are altered by immobilization, and the activity is attenuated. Methods according to U.S. Pat. No. 3,652,761 are no exception.

SUMMARY OF THE INVENTION

The object of the present invention relates to a method for the immobilization of physiologically active substances on an inorganic support or carrier, by means of which the activity of the physiologically active substance is maintained, and which is capable of generating large immobilization quantities.

DETAILED DESCRIPTION OF THE INVENTION

In accordance with the present invention, an inorganic support is treated with an aminoalkylalkoxysilane having the general formula (1) $(RO)_3SiCH_2CH_2CH_2NH(CH_2)_nNH_2$     (1)

wherein, R is au alkyl group having 1 to 4 carbon atoms, and n is an integer having a value of 5 to 12, and the physiologically active substance is chemically bonded to the support using an amino group.

The inorganic carrier or support includes porous glass, silica gel, colloidal silicas, alumina, kaolinite, bentonite, wollastonite, hydroxyapatite, metal hydroxides, and metal oxides.

In the aminopropylalkoxysilane of formula (1) used to treat such inorganic carriers, R is exemplified by methyl, ethyl, n-propyl, and n-butyl groups. n is an integer with a value from 5 to 12. The aminopropylalkoxysilane of formula (1) is exemplified by:
N-(6-aminohexyl)-3-aminopropyltrimethoxysilane,
N-(6-aminohexyl)-3-aminopropyltriethoxysilane,
N-(8-aminooctyl)-3-aminopropyltrimethoxysilane, and
N-(12-aminododecyl)-3-aminopropyltripropoxysilane.

The aminopropylalkoxysilane of formula (1) is prepared by reaction of a 3-chloropropyltrialkoxysilane with at least 2-fold (molar) of a diamine of the formula $N_2N-(CH_2)_n-NH_2$ wherein, n is an integer with a value of 5 to 12). The evolved hydrochloride is removed followed by purification by distillation in vacuo. Diamines with $n \geq 13$ are not preferred because the corresponding aminopropylalkoxysilanes are difficult to distill in vacuo due to high boiling points. On the other hand, at low n values, a high level of activity by the physiologically active substance will not be maintained, and large immobilization loadings will not be obtained. Accordingly, among the aminopropylalkoxysilanes of formula (1), suitable selections are those with n=at least 6, and Particularly those in which n is an even number (6, 8, or 10).

The aminopropylalkoxysilanes of formula (1) have two different types of functional groups in the same molecule. The alkoxysilane moiety in the molecule has the ability to bond to inorganic supports, while the primary amino group moiety in the molecule has the ability to bond to various physiologically active substances. In other words, the aminopropylalkoxysilane mediates chemical bonding between the inorganic carrier or support and the physiologically active substance. When an aminopropylalkoxysilane of formula (1) is used for the immobilization of physiologically active substance, the chain from the silicon atom to the primary amino group results in little restriction on the higher order structure peculiar to the physiologically active substance as compared to the use of the 3-aminopropyltriethoxysilane or N-(2-aminoethyl)-3-aminopropyltrimethoxysilane used heretofore. Accordingly, the physiological activity is maintained at high levels. Another characteristic arising as a consequence of the chain from the silicon atom to the primary amino group is that the immobilizable quantity or loading of physiologically active substance can be increased.

The physiologically active substance includes enzymes, antibodies, and antigens. A wide range of enzyme species can be used, for example, oxidoreductases, hydrolases, transferases, lyases, isomerases and restriction enzymes. Examples of oxidoreductases are glucose oxidase, catalase, and peroxidase. Examples of hydrolases are proteolytic enzymes such as papain, trypsin, chymotrypsin, and thermolysin; ester hydrolases such as lipase; and ribonucleases such as nuclease. The antibodies and antigens encompass antigens such as the various immunoglobulins, hormones and proteins.

In the immobilization of a physiologically active substance on an inorganic carrier or support, the surface of the inorganic support is treated with aminopropylalkoxysilane of formula (1) using a procedure which is known. Typically, the aminopropylalkoxysilane (1) is dissolved in an organic solvent such as toluene or xylene an the surface of the inorganic support is treated with the solution. Treatment is preferably carried out using a solution with a concentration of 0.1 to 40 weight%, with heating, for example, at 50 to 110 degrees Centigrade, for several hours. In such treatment, the hydroxyl groups present on the surface of the inorganic support undergo an alcohol-liberating condensation with the silicon-bonded alkoxy groups in formula (1). As an alternative, an aqueous solution may be used.

The support, obtained by treatment as above described, is capable of covalently bonding with physiologically active substances based on the primary amino group in formula (1). Standard reactions can be used. For example, highly reactive aldehyde groups can be introduced by treatment with a dialdehyde such as glutaraldehyde, followed by bonding with the physiologically active substance. Alternatively, aromatic amino groups can be introduced by treatment with para-nitrobenzoyl chloride followed by reduction, and bonding with the physiologically active substance is carried out after diazotization or via the hydrazine derivative. In another approach, the carboxyl group is introduced by treatment with a carboxylic acid anhydride, followed by a dehydration condensation with residual amino groups on the physiologically active substance using carbodiimide.

Procedures for bonding between the physiologically active substance and the primary amino group in formula (1) bonded on the inorganic support consist of the use of an aqueous medium at a temperature and PH not tending to inactivate the physiologically active substance. In such procedures for the immobilization of physiologically active substances, a bonding strategy is selected which relies on residual groups in the physiologically active substance which are not essential to the activity of the physiologically active substance. For example, residual reactive groups which may be available on an enzyme (globular protein) in regions isolated from the active center are: the epsilon-amino group of lysine and the N-terminal amino group; the sulfhydryl group of cysteine; the residual carboxyl group on aspartic acid and glutamic acid and the C-terminal carboxyl group; the phenolic hydroxyl group on tyrosine; the hydroxyl groups of serine and threonine; the guanidine group in arginine; the imidazole group in histidine; the indole group in tryptophan; and the thioether group in methionine; with the proviso that the active region of the enzyme be considered, and amino groups, carboxyl groups, and hydroxyl groups used as reactive groups due to high content.

In the chemical bonding of physiologically active substance to the inorganic support, as a consequence of the length of the chain in the residual group of the aminopropylalkoxysilane of formula (1) which functions as an intermediary in the bonding; the immobilization method of the present invention characteristically affords an immobilization in which the higher order structure of the physiologically active substance is preserved and a high level of activity is maintained.

Physiologically active substances immobilized on an inorganic support obtained by means of the present invention can be used in a number of applications, for example, in bioreactors, enzyme sensors, immunosensors, radioimmunoassay, chemical analysis, clinical investigations, and medical treatment.

EXAMPLE 1

Silica gel of particle size 10 micrometers and a specific surface area of 100 m$^2$/g was added to a 10 weight% toluene solution of N-(8-aminooctyl)-3-aminopropyltrimethoxysilane, and silane treatment was carried out by heating for 3 hours at 100 degrees Centigrade. After washing with methanol and ion-exchanged water, the silica gel was placed in a 5 weight% aqueous solution of glutaraldehyde and stirred for 4 hours in order to introduce the aldehyde group This was followed by another wash with ion-exchanged water.

Glucose oxidase was immobilized on the silica gel by placing it in 0.05 M sodium acetate buffer containing 2 g/L glucose oxidase, reacting for 12 hours, and washing with a buffer.

The activity of the immobilized enzyme was determined by adding it to a mixture of 2.4 mL of the above buffer containing 0.21 mM ortho-dianisidine, 0.5 mL 10% (w/v) aqueous D-glucose, and 0.1 mL aqueous peroxidase (60 U/mL), and by measuring the absorbance change at 500 nanometers. The activity of the silica gel-immobilized glucose oxidase was 3.0 U per 1 gram of carrier.

COMPARISON EXAMPLE 1

Glucose oxidase was immobilized on silica gel under the same conditions as in Example 1, but using 3-aminopropyltriethoxysilane instead of the N-(8-aminooctyl)-3-aminopropyltrimethoxysilane used in Example 1. The activity of the silica gel-immobilized glucose oxidase was 1.8 U per 1 gram of carrier.

EXAMPLE 2

A porous glass powder with 610 angstrom pores and 0.53 cc/g pore volume was added to a 7 weight% toluene solution of N-(6-aminohexyl)-3-aminopropyltrimethoxysilane, and silane treatment was carried out by heating for 3 hours at 102 degrees Centigrade. The silane-treated porous glass powder was washed with toluene, methanol, and dried in vacuo. It was placed in a 16.7 weight% aqueous solution of glutaraldehyde, stirred for 2 hours in order to introduce aldehyde groups, and washed with ion-exchanged water.

The product was added to a buffer (pH 7.5) of 5 M NaBr, 16.6 mM CaCl$_2$, and 0.025 M Tris-HCl which contained 10 g/L thermolysin. The thermolysin was immobilized on the porous glass powder by stirring overnight at room temperature. After washing in 16.6 mM CaCl$_2$, 0.025 M Tris-HCl buffer, it was placed for 15 minutes in 1 weight% aqueous NaBH$_4$ solution to afford a porous glass powder-immobilized thermolysin.

The activity of the immobilized enzyme for dairy casein at 35 degrees Centigrade was calculated. One unit was selected as the quantity of enzyme producing an increase in nonprotein Folin color corresponding to 1 Mmol tyrosine, in the initial one minute of the reaction. The activity of the immobilized enzyme was 1.87 U per 1 gram of carrier.

COMPARISON EXAMPLE 2

Thermolysin was immobilized on porous glass powder under the same conditions as in Example 2, with the exception that N-(2-aminoethyl)-3-aminopropyltrimethoxysilane was used in place of the N-(6-aminohexyl)-3-aminopropyltrimethoxysilane used in Example 2. The activity of the immobilized enzyme was 0.66 U per 1 gram of carrier.

EXAMPLE 3

A microfine magnetite was prepared by adding 20 weight% aqueous sodium hydroxide to pH 11.5 to an aqueous solution containing 0.25 mol/L ferrous chloride and 0.50 mol/L ferric chloride, followed by ageing for 2 minutes at 60 degrees Centigrade. The alkali and electrolyte were removed by repetitive decantation using ion-exchanged water. The average diameter of the obtained magnetite was 100 angstroms as measured by TEM.

N-(6-aminohexyl)-3-aminopropyltrimethoxysilane was added to a concentration of 10 weight% to the suspension of magnetite, and silane treatment was conducted by heating for 3 hours at 95 degrees Centigrade. After washing the silane-treated magnetite with ion-exchanged water, it was placed in a 10 weight% aqueous solution of glutaraldehyde and stirred for 4 hours in order to introduce the aldehyde group; followed by washing with ion-exchanged water.

The product was added to a buffer (pH 7.5) of 5 M NaBr, 16.6 mM $CaCl_2$, and 0.025 M Tris-HCl containing 10 g/L thermolysin, and the thermolysin was immobilized on the magnetite by stirring overnight at room temperature. Washing was carried out using 16.6 mM $CaCl_2$, 0.025 M Tris-HCl buffer.

The dispersing liquid for the thermolysin-immobilizing magnetite was replaced with ethanol containing 2 weight% of the buffer, and then with ethyl acetate containing 2 weight% of the buffer. Dipeptide (N-Cbz-L-aspartyl-L-phenylalanine methyl ester) synthesis was carried out by the addition of N-Cbz-L-aspartic acid and L-phenylalanine methyl ester to concentrations of 80 mM and 160 mM, respectively, and shaking at 40 degrees Centigrade.

After two hours, the enzyme-immobilizing magnetite was magnetically separated from the dispersing liquid, and the quantity of dipeptide product was investigated using HPLC. 0.3 mmol dipeptide was produced per 1 gram of the magnetite carrier.

EXAMPLE 4

Glutaric anhydride was added to a concentration of 3 weight% to the suspension of silane-treated magnetite as described in Example 3. This was stirred in order to convert the amino group terminal of the silane to a carboxylic group terminal; followed by washing with ion-exchanged water.

To 2 mL of a suspension of magnetite having carboxyl group terminals was added 2 mL buffer containing 1-ethyl-3-(3-dimethylaminopropyl)carbodiimide at a concentration of 60 mg/L and thermolysin at a concentration of 10 g/L. The thermolysin was immobilized on the magnetite by shaking for 3 hours. Washing was carried out using 16.6 mM $CaCl_2$, 0.025 M Tris-HCl buffer.

The dispersing liquid was replaced for the product using the same procedure as in Example 3. When the dipeptide synthesis reaction was conducted, 0.25 mmol dipeptide was produced per 1 gram of magnetite carrier.

EXAMPLE 5

Anti-human IgG was immobilized by the addition of anti-human IgG to the suspension of aldehyde group-containing magnetite of Example 3, shaking for 5 hours, and washing. The quantity of anti-human IgG immobilized was calculated by the Lowry method of the quantity of IgG remaining in the wash solution 50 mg anti-human IgG was immobilized per 1 gram of magnetite.

The product was used to determine the quantity of IgG in a sample by means of addition to a liquid mixed sample containing labelled IgG and IgG, competitive binding with the antibody, and magnetically conducting a B/F separation.

In the immobilization of physiologically active substance on an inorganic carrier or support, as a consequence of the suitable length of the chain in the residual group of the aminopropylalkoxysilane of formula (1) which functions as an intermediary in the bonding between the physiologically active substance and inorganic support, the method of the present invention maintains a high level of activity on the part of the physiologically active substance while also affording high quantities of immobilization.

What is claimed is:

1. A method of immobilizing physiologically active substances on an inorganic support comprising treating an inorganic support with an aminoalkylalkoxysilane selected from the group consisting of N-(8-aminooctyl)-3-aminopropyltrimethoxysilane and N-(12-aminododecyl)-3-aminopropyltripropoxysilane, and chemically bonding said physiologically active substance by means of an amino group to said support.

2. The method of claim 1 wherein the physiologically active substance is an enzyme.

3. The method of claim 1 wherein the physiologically active substance is selected from the group consisting of antibodies and antigens.

4. The method of claim 1 wherein said aminoalkylalkoxysilane is N-(8-aminooctyl)-3-aminopropyltrimethoxysilane.

5. The method of claim 1 wherein said aminoalkylalkoxysilane is N-(12-aminododecyl)-3-aminopropyltripropoxysilane.

6. The method of claim 4 or 5 wherein the physiologically active substance is selected from the group consisting of antibodies and antigens.

7. The method of claim 4 or 5 wherein the physiologically active substance is an enzyme.

* * * * *